US010736646B2

(12) United States Patent
Chu (10) Patent No.: US 10,736,646 B2
(45) Date of Patent: Aug. 11, 2020

(54) STONE CAPTURE DEVICES AND METHODS (71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 165 days.

(21) Appl. No.: 15/883,353

(22) Filed: Jan. 30, 2018

(65) Prior Publication Data

US 2018/0221035 A1 Aug. 9, 2018

Related U.S. Application Data (60) Provisional application No. 62/455,355, filed on Feb. 6, 2017.

(51) Int. Cl.
*A61B 17/221* (2006.01)
*A61B 17/00* (2006.01)
*A61B 1/018* (2006.01)
*A61B 90/00* (2016.01)

(52) U.S. Cl.
CPC ............ *A61B 17/221* (2013.01); *A61B 1/018* (2013.01); *A61B 2017/0034* (2013.01); *A61B 2017/0046* (2013.01); *A61B 2017/00367* (2013.01); *A61B 2017/00424* (2013.01); *A61B 2017/00455* (2013.01); *A61B 2090/0811* (2016.02)

(58) Field of Classification Search
CPC .......... A61B 17/221; A61B 2017/0034; A61B 2017/00367; A61B 2017/00424; A61B 2017/00455; A61B 2017/0046; A61B 2090/0811
See application file for complete search history.

(56) References Cited

U.S. PATENT DOCUMENTS

| 4,763,668 | A | 8/1988 | Macek et al. |
| 5,501,692 | A * | 3/1996 | Riza ................... A61B 17/0469 112/169 |
| 6,059,796 | A | 5/2000 | Bilitz et al. |
| 6,540,722 | B1 | 4/2003 | Boyle et al. |
| 8,523,879 | B1 | 9/2013 | Lind et al. |
| 9,192,402 | B2 | 11/2015 | Galperin et al. |
| 2005/0075656 | A1* | 4/2005 | Beaupre ................. A61B 17/11 606/153 |
| 2013/0211427 | A1* | 8/2013 | Castell Gomez .. A61B 17/0401 606/144 |

* cited by examiner

*Primary Examiner* — Jocelin C Tanner
(74) *Attorney, Agent, or Firm* — Bookoff McAndrews, PLLC (57) ABSTRACT

Aspects of a device are described herein. The device may comprise: a housing including a track with a plurality of segments; a plunger including a pin located in the track; a sheath extending distally from the housing; a wire extending distally from the plunger into the sheath; and an end effector on a distal end of the wire, wherein the housing is movable relative to the plunger to move the pin between the plurality of segments, and each of the plurality of segments corresponds with a position of the end effector relative to the sheath. Related devices, kits, and methods also are disclosed.

20 Claims, 8 Drawing Sheets

```
200
 ↓
┌─────────────────────────────────────────────────────────────────────┐
│ STEP 210: CONFIGURING A DEVICE INCLUDING A HOUSING WITH A TRACK, A  │
│ PLUNGER WITH A PIN LOCATED IN THE TRACK, A SHEATH EXTENDING         │
│ DISTALLY FROM THE HOUSING, A WIRE EXTENDING DISTALLY FROM THE       │
│ PLUNGER, THROUGH THE HOUSING, AND INTO THE SHEATH, AND AN END       │
│ EFFECTOR ON A DISTAL END OF THE WIRE                                │
└─────────────────────────────────────────────────────────────────────┘
                                  ↓
┌─────────────────────────────────────────────────────────────────────┐
│ STEP 220: POSITIONING A DISTAL END OF THE SHEATH ADJACENT A STONE   │
│ IN A BODY CAVITY                                                    │
└─────────────────────────────────────────────────────────────────────┘
                                  ↓
┌─────────────────────────────────────────────────────────────────────┐
│ STEP 230: MOVING THE HOUSING RELATIVE TO THE PLUNGER TO MOVE THE PIN│
│ THROUGH THE TRACK UNTIL THE END EFFECTOR EXTENDS FROM THE DISTAL    │
│ END OF THE SHEATH TO ASSUME AN OPEN STATE                           │
└─────────────────────────────────────────────────────────────────────┘
                                  ↓
┌─────────────────────────────────────────────────────────────────────┐
│ STEP 240: AT LEAST PARTIALLY SURROUNDING THE STONE WITH THE END     │
│ EFFECTOR                                                            │
└─────────────────────────────────────────────────────────────────────┘
                                  ↓
┌─────────────────────────────────────────────────────────────────────┐
│ STEP 250: MOVING THE HOUSING RELATIVE TO THE PLUNGER TO MOVE THE PIN│
│ THROUGH THE TRACK UNTIL THE END EFFECTOR CLOSSES ABOUT THE STONE    │
└─────────────────────────────────────────────────────────────────────┘
                                  ↓
┌─────────────────────────────────────────────────────────────────────┐
│ STEP 260: MOVING THE HOUSING RELATIVE TO THE PLUNGER TO MOVE THE PIN│
│ THROUGH THE TRACK UNTIL THE PIN IS LOCATED IN A SEGMENT OF THE      │
│ TRACK CONFIGURED TO PREVENT FURTHER CLOSURE OF THE END EFFECTOR     │
└─────────────────────────────────────────────────────────────────────┘
```

*FIG. 8*

STONE CAPTURE DEVICES AND METHODS

CROSS-REFERENCE TO RELATED APPLICATION(S)

This patent application claims the benefit under 35 U.S.C. § 119 to U.S. Provisional Patent Application No. 62/455,355, filed on Feb. 6, 2017, the entirety of which is incorporated herein by reference.

TECHNICAL FIELD

Aspects of the present disclosure generally relate to medical devices and procedures. Particular aspects relate to stone capture devices and methods.

BACKGROUND

Various retrieval devices may be used to remove a targeted object (e.g., a kidney stone) from a portion of a body (e.g., the interior portion of a kidney). Some retrieval devices may include a flexible sheath configured for delivery through a working channel of an insertion device, and an end effector deployable from a lumen of the flexible sheath. Exemplary insertion devices may include an endoscope or a ureteroscope; and exemplary end effectors may include an expandable basket. Some end effectors may include a wire extending through the lumen of the sheath, and an expandable basket attached to a distal end of the wire. The basket may be closed into a the lumen when the sheath is moved distally relative to the wire, and opened out the lumen when the sheath is moved proximally. Over time, these reciprocal movements may cause damage to the device or otherwise complicate the stone retrieval process. For example, the end effector may break or otherwise be damaged if too much movement force is applied to the sheath. Even with normal movement forces, sheath compression may occur, wherein the sheath becomes shorter over time unit it cannot extend distally to close the end effector entirely, making it difficult to capture smaller stones.

The risk of damage and/or malfunction from reciprocal movements increases when the sheath is placed in a tortuous path. For example, the sheath may be snaked through a body path including curves and/or twists, such as a path extending from the urethra, through the bladder and ureter, around the renal pelvis, and into or out of a particular calyx of a kidney. Such a path may shift the lumen relative to the wire, causing the wire to hug the inner radius of curved portions of the lumen of the sheath, and lengthening the wire relative to the sheath. The resulting mismatch or offset in the sheath and wire lengths may prevent the end effector from closing completely, again making it difficult to capture smaller stones.

The devices and methods disclosed herein may remedy one or more of the aforementioned difficulties of capturing smaller stones, and/or address other aspects of the prior art.

SUMMARY

One aspect of the present disclosure is a device. An exemplary device may comprise: a housing including a track with a plurality of segments; a plunger including a pin located in the track; a sheath extending distally from the housing; a wire extending distally from the plunger into the sheath; and an end effector on a distal end of the wire. The housing may be moveable relative to the plunger to move the pin between the plurality of segments of the track, and each of the plurality of segments may correspond with a position of the end effector relative to the sheath.

According to this aspect, the plurality of segments may comprise: a distal segment, at which the pin is located to fully extend the end effector from the sheath; a central segment, at which the pin is located to partially extend the end effector from the sheath; and a proximal segment, at which the pin is located to fully retract the end effector into the sheath. The central segment may comprise a central linear segment. The distal segment may comprise a distal offshoot transverse to and distal of the central linear segment. The pin may be moveable into the distal offshoot to maintain the end effector in the fully open state. The central linear segment may comprise at least one central offshoot extending away from the central linear segment. The pin may be movable into the at least one central offshoot to maintain the end effector in a partially open state. For example, the end effector may assume a predetermined open size when the pin is moved into the at least one central offshoot.

The central linear segment may terminate proximally in a seat. The end effector may assume a fully closed state when the sheath is in a first configuration and the pin is moved into the seat. The proximal segment may comprise a proximal offshoot extending transverse to and proximally of the seat. The end effector may assume the fully closed state when the sheath is in a second configuration and the pin is moved into the proximal segment. The second configuration may be more tortuous than the first configuration. A perimeter of the track may be symmetrical about a longitudinal axis of the housing. The device may comprise an elastic member configured to bias the housing away from the plunger. For example, the elastic member may be a spring configured to apply a biasing force, and the biasing force may vary depending upon the position of the housing relative to the plunger.

In some aspects, the pin may extend outwardly from a side surface of the plunger, and the side surface may be configured to bias the pin into the track. The wire may be removably engageable with a proximal end of the plunger. The proximal end of the plunger may be removably engageable with at least one of a scope and a removable handle. A distal end of the housing may include a handle.

Another aspect of the present disclosure is another device. This exemplary device may comprise: a plunger that includes a pin and is engageable with a wire having a distal end; a housing that is engageable with a sheath, configured to receive the plunger, and includes a track having a plurality of segments, wherein the pin is located in the track and the housing is movable relative to the plunger such that: the pin is movable through the track to guide movement of the plunger relative the housing; the wire extends distally from the plunger, through the housing, and into the sheath; and each of the plurality of segments corresponds with a position of the end effector relative to the sheath.

In this aspect, a central segment of the plurality of segments may comprise a at least one central offshoot transverse to a longitudinal axis of the housing, and the pin may be engageable with the at least one offshoot to maintain the end effector in a partially open state. A perimeter of said offshoot may be symmetrical with respect to the longitudinal axis so that the housing is rotatable in a clockwise or a counterclockwise direction relative to the plunger to locate the pin in said at least one central offshoot. The pin may extend outwardly from a side surface of the plunger, and the side surface may be configured to bias the pin toward the track. A proximal end of the wire may be attached to a proximal end of the plunger, and the proximal end of the plunger may be removably engageable with at least one of a scope and a handle. In some aspects, a proximal segment of the plurality of segments may comprise a proximal offshoot extending transverse to and proximally of the seat, the end effector may assume the fully closed state when the sheath is in a second configuration and the pin is moved into the proximal segment, and the second configuration may be more tortuous than the first configuration.

Yet another aspect of the present disclosure is a kit comprising any device described herein, a length of the wire; and a length the sheath. An exemplary kit may further include a handle removably engageable with the proximal end of the plunger.

Still yet another aspect of the present disclosure is a method. An exemplary method may comprise using a device including a housing with a track, a plunger including a pin located in the track, a sheath extending distally from the housing, a wire extending distally from the plunger, through the housing, and into the sheath, and an end effector on a distal end of the wire. This method may comprise: moving the housing relative to the plunger to move the pin through the track until the end effector extends from the sheath to assume an open state; at least partially surrounding a stone with the end effector; moving the housing relative to the plunger to move the pin through the track until the end effector closes about the stone; and moving the housing relative to the plunger to move the pin through the track until the pin is located in a segment of the track configured to prevent further closure of the end effector.

In this method, the device may further include an elastic member configured to bias the housing away from the plunger, and moving the housing relative to the plunger may comprise compressing the elastic member. The method may further comprise releasing the stone by moving the housing relative to the plunger to move the pin through the track until the end effector extends from the sheath lumen opening to assume the open state. In some aspects, the method may comprise: advancing the sheath through a body path; and positioning a distal end of the sheath lumen opening adjacent the stone. The method may further comprise attaching one of the housing or the plunger to a scope.

It is understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more exemplary aspects according to this disclosure, as follows.

DETAILED DESCRIPTION

Aspects of the present disclosure are now described with reference to exemplary devices, methods, and systems for stone capture. Specific aspects are described with reference to medical procedures where a retrieval device is utilized to capture a kidney stone located inside the calyx of a kidney. References to a particular type of procedure, such as medical procedure for removing a stone; device, such as a retrieval device; and/or organ, such as a bladder, are provided for convenience and not intended to limit this disclosure. Accordingly, the concepts described herein may be utilized for any analogous method—medical or otherwise. In addition the handles described herein may be used in combination with any end effector that, for example, moves relative to a sheath. The various baskets described herein are exemplary and not intended to be limiting of the present disclosure.

The directional terms "proximal" and "distal," and their respective initials "P" and "D," are utilized herein. Proximal refers to a position closer to the exterior or the body or a user, whereas distal refers to a position closer to the interior of the body or further away from the user. Appending the initials "P" or "D" to an element number signifies a proximal or distal location or direction.

The term "elongated" as used herein refers to any object that is substantially longer in relation to its width, such as an object having a length that is at least two times longer than its width along its longitudinal axis. Some elongated objects, for example, are axially extending in a proximal or distal direction along said axis. Unless claimed, these terms are provided for convenience and not intended to limit this disclosure to a particular location, direction, or orientation.

As used herein, terms such as "comprises," "comprising," or like variations, are intended to cover a non-exclusive inclusion, such that any aspect that comprises a list of elements does not include only those elements or steps, but may include other elements or steps not expressly listed or inherent thereto. Unless stated otherwise, the term "exemplary" is used in the sense of "example" rather than "ideal." Conversely, the terms "consists of" and "consisting of" are intended to cover an exclusive inclusion, such that an aspect that consists of a list of elements includes only those elements. As used herein, terms such as "about," "substantially," "approximately," or like variations, may indicate a range of values within +/−5% of a stated value.

Figure 1:
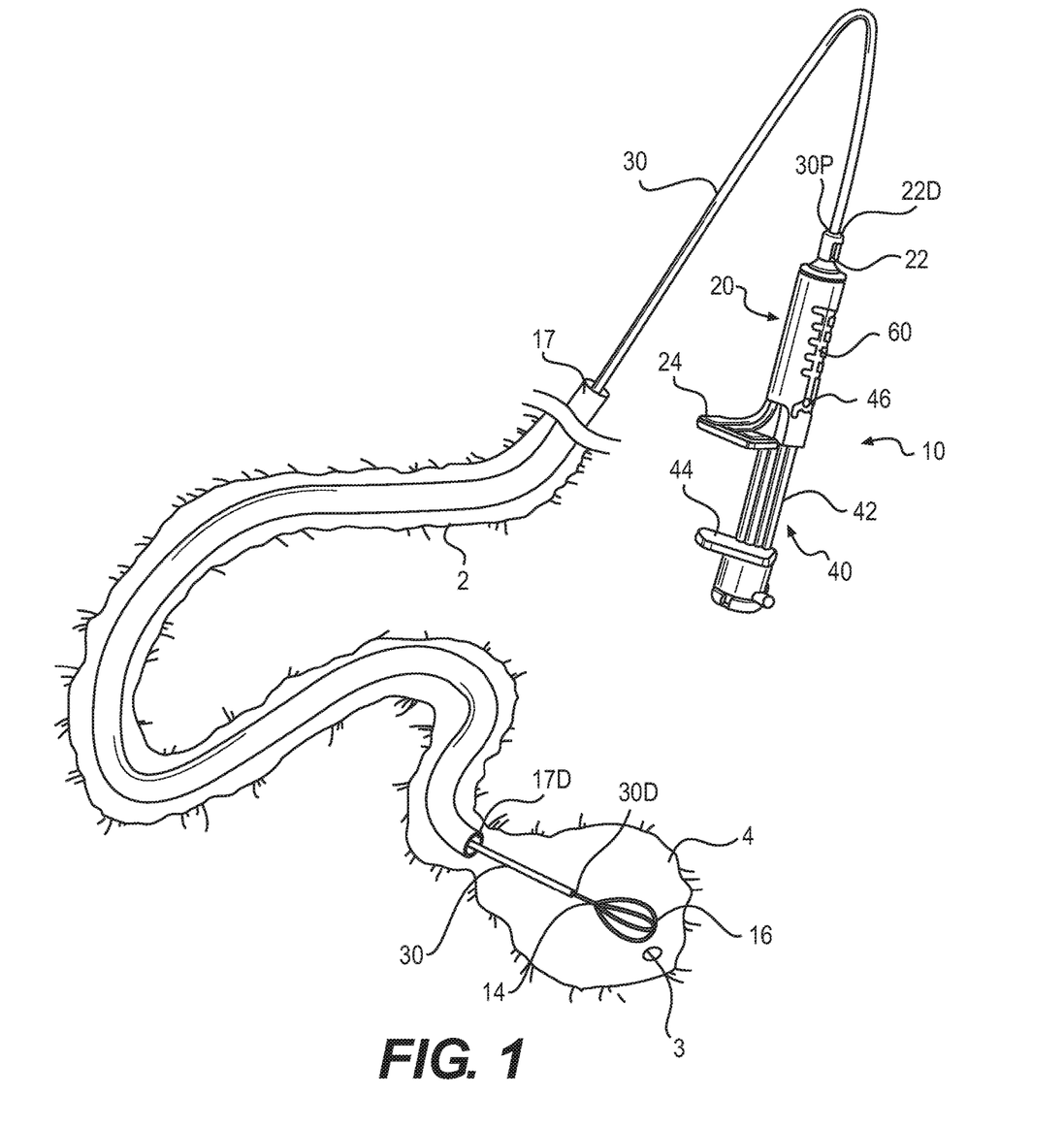
FIG. 1 depicts an exemplary retrieval device.

An exemplary device 10 is now described with reference to FIGS. 1-5. As shown in FIG. 1, device 10 may comprise: a housing 20 including a track 60; a plunger 40 including a pin 46 located in track 60; a sheath 30 extending distally from housing 20; a wire 14 extending distally from plunger 40 through housing 20 into sheath 30; and an end effector 16 on a distal end of wire 14. In this configuration, housing 20 may be movable relative to plunger 40 to move pin 46 in track 60. The interaction of pin 46 with track 60 may guide movement of plunger 40 and wire 14 relative to housing 20 and sheath 30, allowing end effector 16 to expand from or retract into sheath 30. Additional aspects of device 10 are now described in detail, followed by exemplary methods of use. As shown in FIG. 1, some aspects of device 10 are described with reference to a body path 2 leading to a body cavity 4 with a stone 3 contained therein.

Figure 2A:
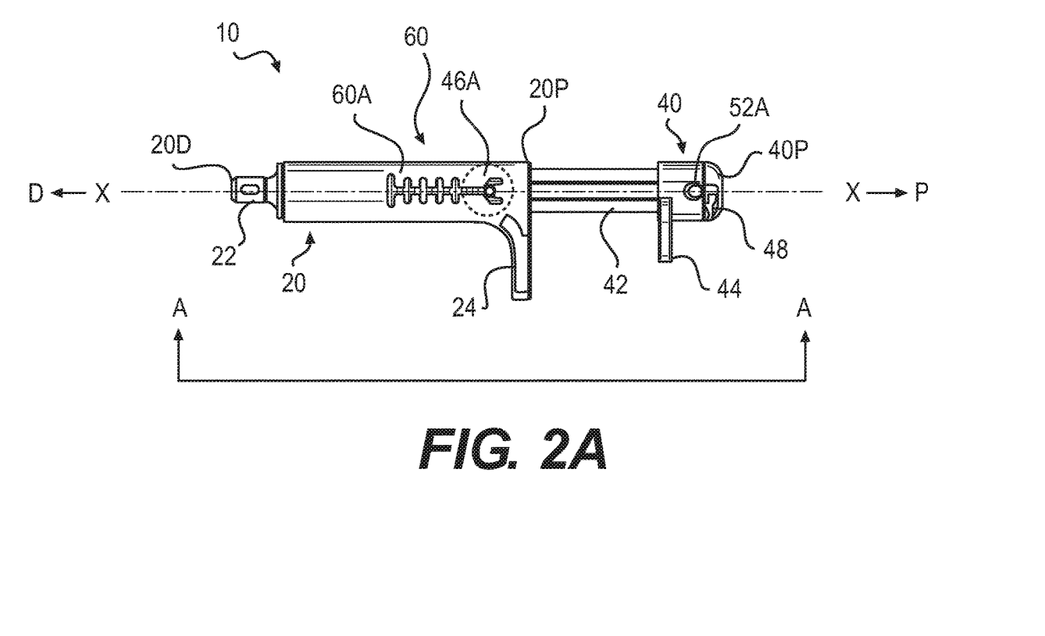
FIG. 2A depicts a side view of a handle of an exemplary retrieval device.

As shown in FIG. 2A, housing 20 may extend along a longitudinal axis X-X between a distal end 20D and a proximal end 20P. Housing 20 may be composed of a polymeric material (e.g., ABS, PEEK, or similar material). Distal end 20D of housing 20 may be removably engageable with, or otherwise affixed to, a proximal end 30P of sheath 30. Any means of attachment is contemplated, chemical and/or mechanical. For example, an outer diameter of distal end 20D may be receivable within an inner diameter of proximal end 30P (or vice versa), allowing end 30P to be fit over (or within) and/or attached to (e.g., by a chemical adhesive) distal end 20D. Sheath 30 may be composed of a biocompatible material (e.g., sheath 30 may be a stainless steel braided polyimide tube, which may have a PFTE coating), allowing distal end 30D to be advanced directly through body path 2. As shown in FIG. 1, sheath 30 also may be advanced through body path 2 in a working channel 17 of a insertion device, such as a scope (e.g., an endoscope) that has been previously advanced through path 2. An exemplary scope may include those sold by Boston Scientific®, such a ureteroscope sold under the brand name LithoVue®.

Figure 2B:
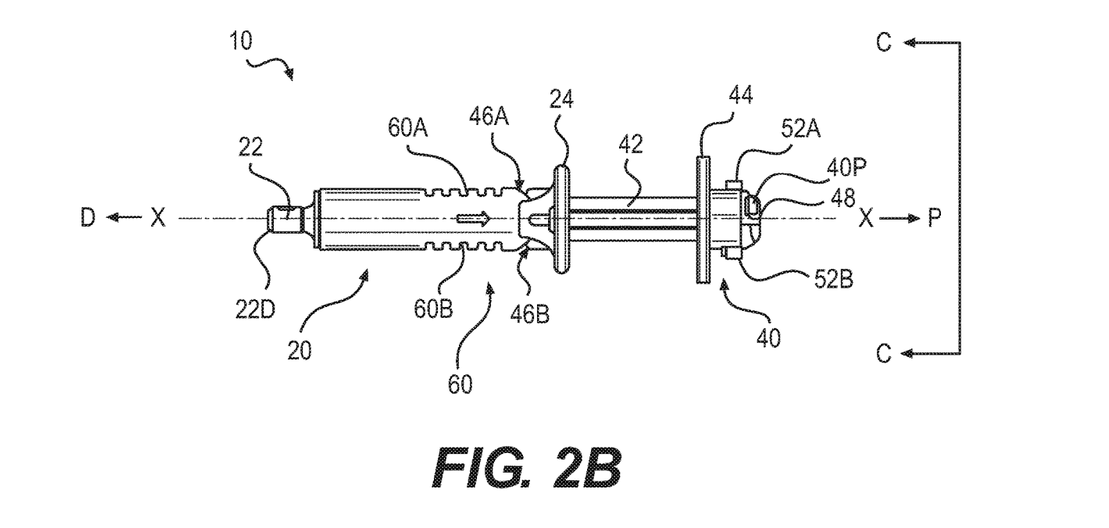
FIG. 2B depicts a side view of the FIG. 2A device along a line A-A.

Housing 20 includes track 60. Pin 46 of plunger 40 is receivable in track 60 to guide relative movements between housing 20 and plunger 40, and/or fix the relative positions of housing 20 and plunger 40. Any number of tracks 60 and pins 46 may be provided. For example, as shown in FIG. 2B, track 60 may include a first track 60A and a second track 60B extending from opposite sides of housing 20 (e.g., 180° apart). First and second tracks 60A and 60B of FIG. 2B may be mirror-images of one another, each being configured to receive a corresponding pin 46A and 46B extending outwardly from plunger 40. In this configuration, tracks 60A and 60B provide numerous guiding surfaces positioned to enhance stability and prevent cocking or the tilting of housing 20 relative to plunger 40. Additional aspects of track 60 and pin 46 are now described without direct reference to track 60A and 60B or pin 46A and 46B, although any aspect of track 60 or pin 46 is interchangeable therewith.

Figure 4A:
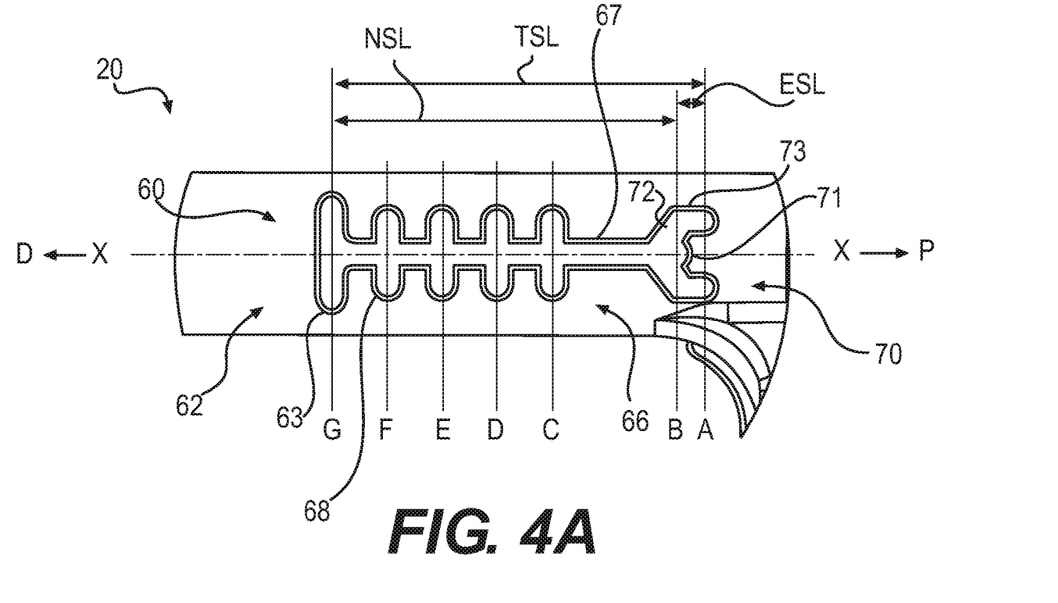
FIG. 4A depicts a close-up view of an exemplary track of the FIG. 2A device.
Figure 4B:
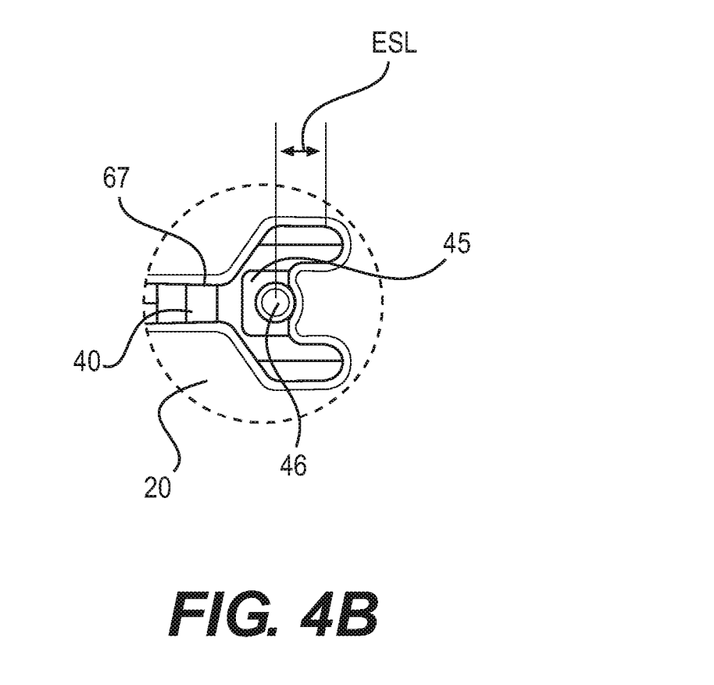
FIG. 4B depicts a close-up view of a portion of the FIG. 4A track located within a circle B in FIG. 2A after a pin has been located therein.

An exemplary track 60 is depicted in FIG. 4A as including a plurality of segments. Each segment of track 60 may correspond with an open or closed state of end effector 16, as described below. As shown in FIG. 4A, track 60 may define a perimeter that is symmetrical about longitudinal axis X-X. For example, as shown, track 60 includes two halves centered on axis X-X, with a first half above axis X-X, and a second half below. These first and second halves enhance the usability of device 10 by providing ergonomic rotational use of device 10 with either hand. For example, track 60 of FIG. 4A is configured such that pin 46 may be moved into a central offshoot 68 located at reference line C, for example, by rotating housing 20 relative to plunger 40 in a clockwise or counterclockwise direction. Because track 60 has a symmetrical shape, rotation of housing 20 in either direction evokes the same response of the end effector.

Figure 5:
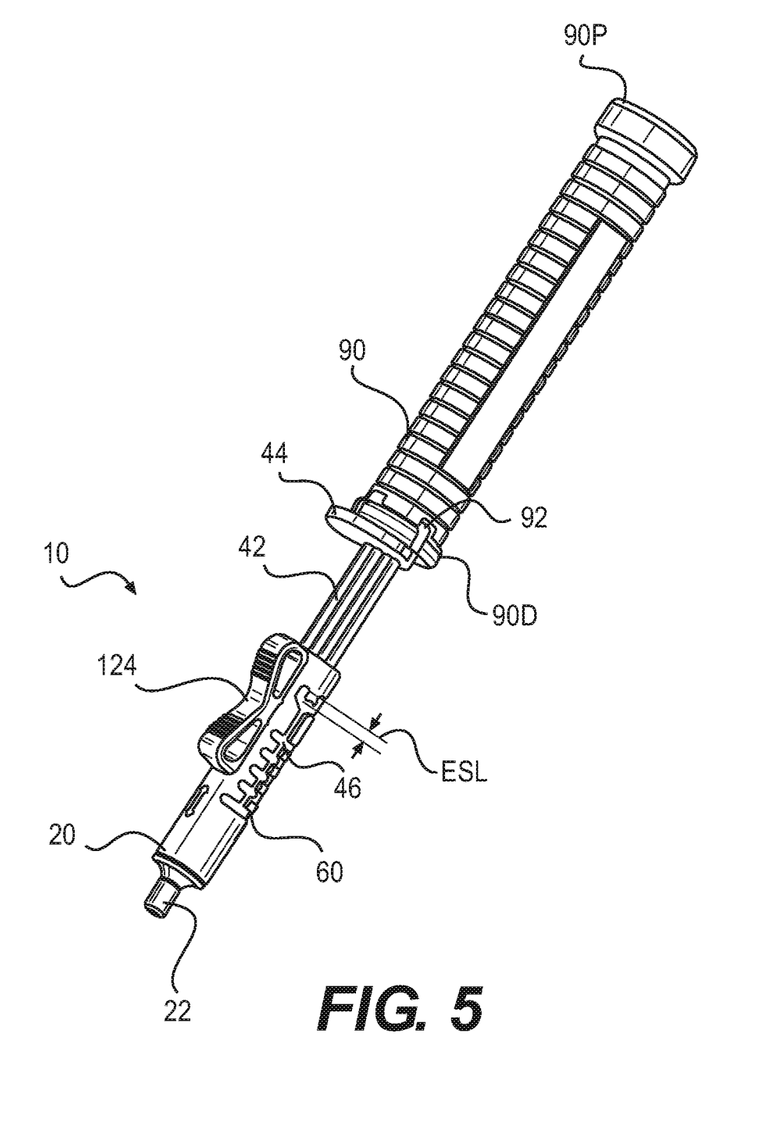
FIG. 5 depicts a perspective view of a handle of another exemplary retrieval device.

As shown in FIGS. 2A-B, proximal end 20P of housing 20 is configured to receive a distal end 40D of plunger 40. For example, proximal end 20P may define an opening, and distal end 40D of plunger 40 (e.g., FIG. 3A) may be movably mounted in the housing 20 when inserted through said opening. Movements between housing 20 and plunger 40 may be guided by interaction of their respective interior and exterior surfaces, providing the user with tactile feedback. Housing 20 further comprises a handle 24 that, as shown in FIG. 2A, extends away from housing 20 (e.g., in a direction transverse with longitudinal axis X-X) at proximal end 20P. Handle 24 may be sized and shaped for use with a hand, allowing for operation of device 10 in view of track 60. For example, a force may be applied to handle 24 by the hand (e.g., with the index finger) to rotate housing 20 in a clockwise or counterclockwise direction about longitudinal axis X-X, and/or move housing 20 in a proximal-distal direction along axis X-X, as required to move pin 46A through track 60A. Handle 24 of FIG. 3C includes directional arrows, and may include other indicators, such as a measurement strip. Any shape for handle 24 may be used, include the shape of the alternate handle 124 that is depicted in FIG. 5 and described further below.

Figure 3A:
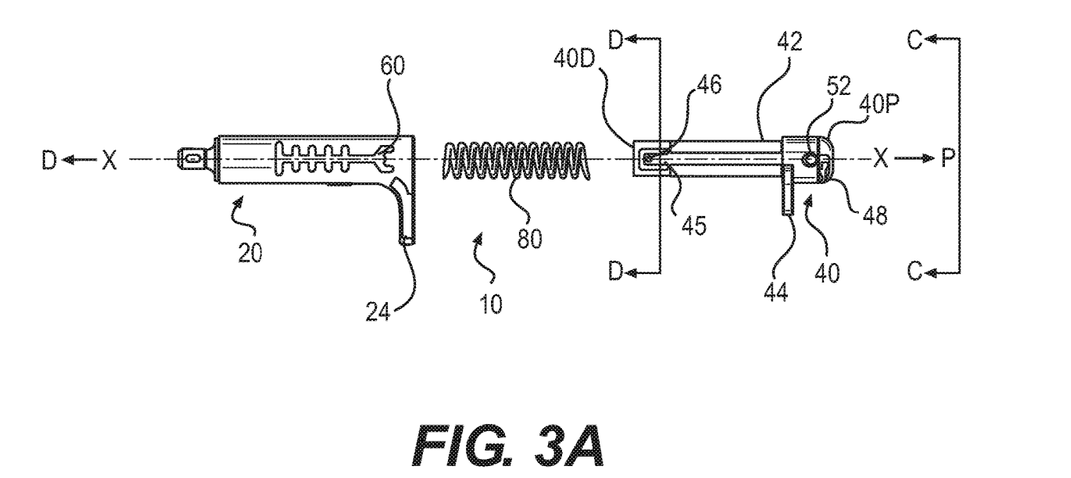
FIG. 3A depicts an exploded view of the FIG. 2A device.
Figure 3B:
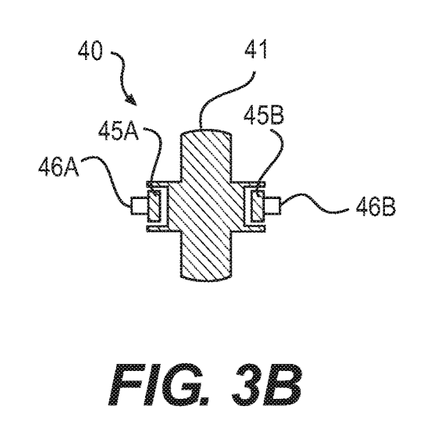
FIG. 3B depicts a cross-sectional view of the FIG. 3A device along a line D-D.

As shown in the exploded view provided by FIG. 3A, plunger 40 may comprise a plunger body 42 extending along longitudinal axis X-X between a distal end 40D and a proximal end 40P. Plunger 40 may be composed of a polymeric material (e.g., ABS, PEEK, or similar material) similar or different to that of housing 20. An exemplary cross-sectional area of plunger body 42 is depicted in FIG. 3B, wherein plunger body 42 is configured for receipt within an opening formed in the proximal end 20P of housing 20. Said opening may provide one or more surfaces configured to guide relative movements between housing 20 and plunger 40. For example, plunger 40 of FIG. 3B has a plus-sign cross-sectional shape that is received in a circular opening extending through proximal end 20P along longitudinal axis X-X. As shown, said shape may have curved outer surfaces configured to guide proximal-distal and/or rotational movements of outer surfaces of plunger 40 relative to interior surfaces of housing 20.

Pin 46 may extend outwardly from a side surface 45 of plunger 40. As noted above, pin 46 may include one or more of a pair of pins 46A and 46B extending outwardly from opposite side surfaces 45A and 45B of housing 20. Pin 46 of FIG. 3A, for example, extends outwardly from side surface 45 at a location adjacent distal end 40D. Side surface 45 may be configured to locate and maintain pin 46 in track 60. As shown in FIG. 3A, for example, side surface 45 may include a cantilevered portion that deflects when distal end 40D of plunger 40 is passed through proximal end 20D of housing 20, and rebounds when pin 46 is positioned in first track 60. Housing 20 may include one or more interior ramps configured to deflect side surface 45, causing pin 46 to snap into track 60 responsive to a rebound force applied by the cantilevered portion.

Figure 3C:
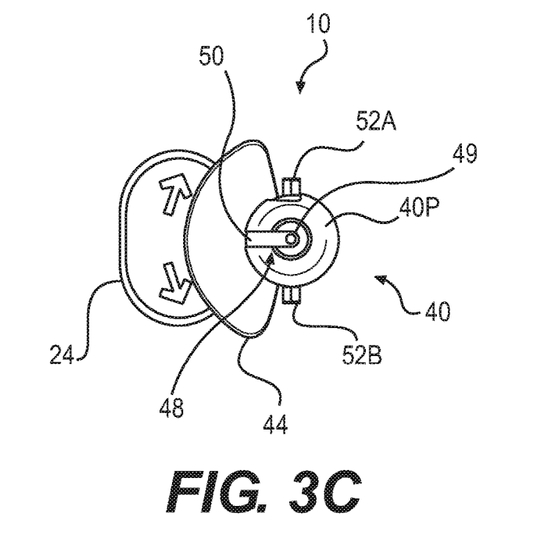
FIG. 3C depicts an end view of the FIG. 3A device along a line C-C.

Proximal end 40D of plunger 40 may comprise a handle 44, a wire engagement structure 48, and a connector structure 52. Handle 44 may, as shown in FIG. 2A, extend away from plunger body 40 (e.g., in a direction transverse with longitudinal axis X-X), and may be sized and shaped for use with a hand. An exemplary wire engagement structure 48 is depicted in FIG. 3C, for example, as including a lumen 49 extending through plunger 40, and catch channel 50 formed on the proximal end 40D of plunger 40. A proximal end of wire 14 may be threaded through lumen 49 in a proximal direction, and then folded into portions of catch channel 50 to attach wire 14 to plunger 40. Proximal portions of wire 14 may be trimmed flush at or below the outer surface of channel 50. Any chemical or physical means (e.g., an adhesive, an epoxy, a screw, or the like) may be used to secure wire 14 within channel 50. Lumen 49 may be sized to receive any number of wires 14 and/or include any number of lumens.

Connector structure 52 attaches device 10 to other devices. For example, connector structure 52 may be configured to attach proximal end 40P to a corresponding connector structure built into a portion of the scope, such as a port. Structure 52 may be configured to interchangeably attach proximal end 40P of plunger 40 to at least one of: the scope or insertion device; a removable operating handle 90 (e.g., FIG. 5); and a scope adapter. This configuration enhances the usability of device 10 by enabling variable modes of operation. For example, engagement structure 52 of FIG. 3C includes a first protrusion 52A and a second protrusion 52B extending away from plunger 40. The scope or insertion device may include a correspondingly shaped groove and/or channel structure engageable with protrusions 52A and 52B to attach device 10, allowing the user to operate end effector 16 by moving housing 20 (e.g., with handle 24) relative to the insertion device.

Removable operating handle 90 of FIG. 5 also includes the corresponding groove and/or channel structure, allowing device 10 to be used interchangeably with handle 90. Plunger 40 also may be formed integral with handle 90. In some aspects, handle 90 may rotate relative to plunger 40 and wire 14, providing additional means for capturing stone 3. Although not shown, device 10 also may be used interchangeability with the scope adapter, which may include a first end engageable with connector structure 52, and a second end engageable with another medical device. The first and second ends may be removably engageable with one another. A plurality of second ends may be provided for use with the scope adapter (e.g., in a kit), and each second end may be engageable with a different medical device to permit greater interchangeability.

Aspects of operating device 10 are now described. For example, the distal end 40D of plunger 40 may be movably mounted in an interior chamber of housing 20 so that pin 46 is positioned in track 60. In this configuration, pin 46 is movable between segments of track 60 to guide movement of plunger 40 and wire 14 relative to housing 20 and sheath 30, allowing end effector 16 to extend from or retract into sheath 30. Interior surfaces of housing 20 may obtain a friction fit with exterior surfaces of plunger 40, providing the user with tactile feel when moving housing 20 relative to plunger 40, and providing controlled movements therebetween.

Track 60 includes a plurality of segments configured to capture and/or release stones 3 of varying types, including smaller and/or softer stones. The plurality of segments are further configured to capture stones 3 when sheath 30 is in a linear or a tortuous configuration. For example, track 60 of FIG. 4A includes a distal segment 62, a central segment 66, and a proximal segment 70. Segments 62, 66, and 70 are arranged along axis X-X to define a total stroke length (or "TSL") extending between a reference line A and a reference line G. To provide relativity between end effector 16 and track 60, the TSL may be equal to a corresponding stroke length of end effector 16, defined as a displacement distance required for moving end effector 16 between an open state (e.g., a fully open state) and a closed state (e.g., a fully closed state). Because of this relativity, pin 46 may be moved along the TSL between segments 62, 66, and 70 to move end effector 16 between open and closed states. For example, pin 46 may be located at: (i) distal segment 62 (e.g., at reference line G) to extend end effector 16 into a fully open state; (ii) central segment 66 (e.g., between reference lines B-G) to extend end effector into a partially open state; and (iii) proximal segment 70 (e.g., at reference line B or A) to retract end effector 16 into a fully closed state.

Distal segment 62 of FIG. 4A comprises a distal offshoot 63 extending away from a central linear segment 67 of central segment 66 along reference line G. By moving housing 20 relative to plunger 40, pin 46 may be located in distal offshoot 63 to maintain end effector 16 in the fully open state. For example, as shown in FIG. 4A, pin 46 may be rotated into distal offshoot 63 in a clockwise or counter clockwise direction to maintain end effector 16. For example, distal offshoot 63 may maintain end effector in the fully open state by engaging pin 46, thereby preventing end effector 16 from being moved back into sheath 30. Distal offshoot 63 (as well as any other offshoot of track 60) may have an axis along reference line G (or the like) that is perpendicular with axis X-X.

Central segment 66 may operate as main slot for track 60A. For example, central linear segment 67 may define a nominal stroke length ("NSL") for track 60 between reference lines B and G. The NSL includes a nominal open and close operating range for end effector 16. Central segment 66 of FIG. 4A includes a plurality of central offshoots 68. In FIG. 4A, for example, one offshoot 68 is located at each of reference lines C, D, E, and F. Pin 46 may be moved into each central offshoot 68 to maintain end effector 16 in a different partially open state.

Central segment 66 may vary according to the configuration of end effector 16 and sheath 30. For example, end effector 16 may be configured to maintain the fully closed state until a proximal portion of end effector 16 is moved distally past the distal end 30D of sheath 30 by a predetermined distance, at which end effector 16 expands or "pops" into the fully open state. The ZeroTip® end effector by Boston Scientific may operate similarly. In this configuration, any central offshoot 68 of track 60 may correspond with the fully open state.

End effector 16 also may be configured to open gradually while being moved distally out of sheath 30. For example, end effector 16 of FIG. 1 may include a plurality of shape memory wires that, when unrestrained by sheath 30, are configured to gradually extend further apart from one another, defining a functionally larger shape as end effector 16 is moved distally. The OptiFlex® end effector by Boston Scientific may operate similarly. In this example, each central offshoot 68 may correspond with a different size or open state of end effector 16. For example, offshoot 68 at reference line C may maintain the smallest size of end effector 16, and offshoots 68 at reference lines D-F may maintain intermediate, progressively larger sizes of end effector 16, and offshoot 63 at line G may the largest size of end effector 16. Each central offshoot 68 may correspond with a different predetermined size of end effector 16 (e.g., 2 mm), and pin 46 may be located at each offshoot 68 to visually compare the size of stone 3 with the one or more of the different predetermined sizes.

Controls may be realized by locating pin 46 at the central offshoots 68 at reference lines C, D, E, and F. For example, pin 46 may be moved between offshoots 68 to incrementally decrease the size end effector 16, allowing for capture of stone 3 from a confined area of body cavity 4 with minimal distortion of end effector 16 from the interior surfaces of cavity 4. As a further example, each central offshoot 68 may correspond with different size of end effector 16, meaning that pin 46 may be located at a first central offshoot 68 to capture stone 3 when end effector 16 assumes a larger size, and then located at one or more subsequent offshoots 68 to incrementally close end effector 16 about stone 3.

Proximal segment 70 aids in retracting end effector 16. For example, proximal segment 70 of FIG. 4A includes a seat 71, and a proximal offshoot 72 extending away from seat 71 to define an extended stroke length (or "ESL") for track 60 between reference lines A and B. Central linear segment 67 terminates at seat 71. If sheath 30 is in a relatively linear configuration, then housing 20 may be moved toward plunger 20 within the NSL to locate pin 46 in seat 71, causing end effector 16 to assume the fully closed state within sheath 30. The length of central linear segment 67 may be insufficient to permit closure of end effector 16 when sheath 30 is in a tortuous configuration due to the resulting offset between sheath 30 and wire 14. Accordingly, if sheath 30 is in a more tortuous configuration, then housing 20 may be moved relative to plunger 40 until pin 46 is moved out of seat 71 and into proximal offshoot 72 along the ESL, allowing end effector 16 to now assume the fully closed state within sheath 30. For example, pin 46 may be moved out of from seat 71 to capture smaller stones with end effector 16 by withdrawing said stones proximally into sheath 30 with end effector 16.

Figure 6:
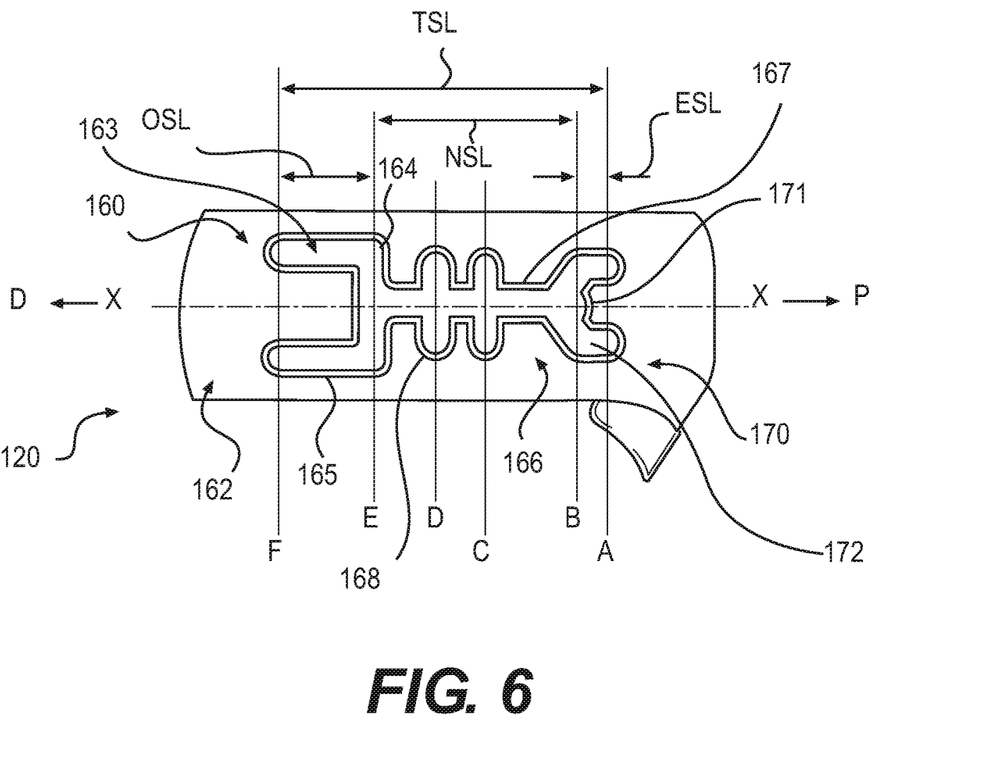
FIG. 6 depicts a close-up view of another exemplary track and pin configuration for the FIG. 2A device.
Figure 7:
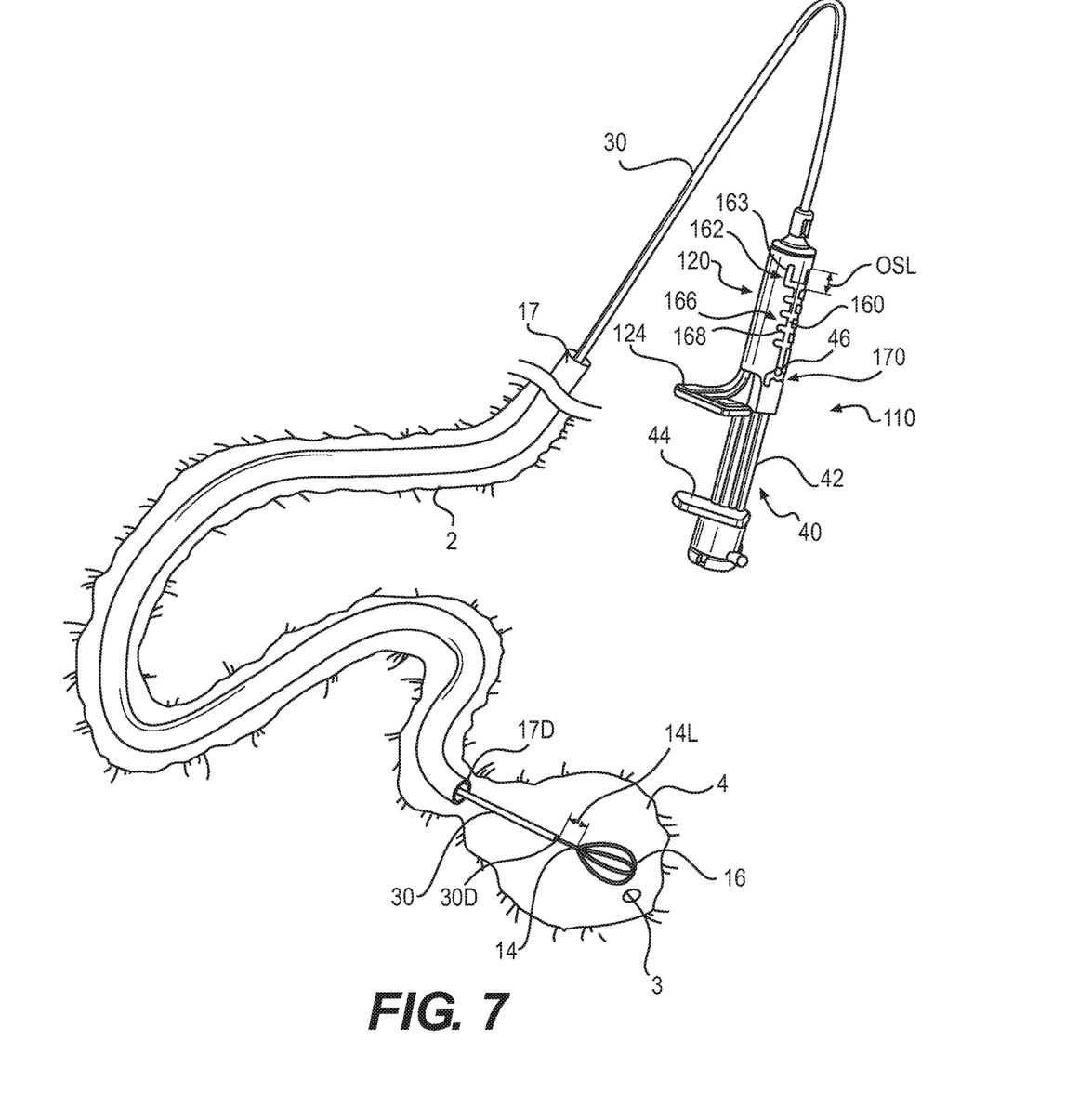
FIG. 7 depicts another exemplary retrieval device.

Additional aspects are now described with reference to an exemplary alternative track 160, examples of which are depicted in FIGS. 6 and 7. Tracks 60 and 160 may be used interchangeably with any aspect of device 10 described herein, as shown in FIG. 7 with reference to a device 110 that is otherwise identical to device 10. Wherever possible, like reference numbers are used to describe like elements of devices 10 and 110, and tracks 60 and 160, but within the 100 series of numbers.

As shown in FIGS. 6 and 7, track 160, like track 60, may comprise a plurality of segments, including a distal segment 162, a central segment 166, and a proximal segment 170. Track 160 is located on housing 20 of FIG. 6, and on housing 120 of FIG. 7, as a direct replacement for track 60. As before, by moving housing 20 relative to plunger 40 (or vice versa), pin 46 may be moved through track 160 between segments 162, 166, and 170 to move end effector 16 between open and closed states. With track 160 of FIG. 6, for example, pin 46 may be located at: (i) distal segment 162 (e.g., between reference lines E-F) to extend end effector 16 into a fully open state; (ii) central segment 66 (e.g., between reference lines B-E) to extend end effector into a partially open state; and (iii) proximal segment 70 (e.g., at reference line B or A) to retract end effector 16 into a fully closed state.

Track 160 is segmented differently than track 60 so as to provide additional means for releasing larger stones 3. For example, as shown in FIG. 6, the TSL for track 160 may extend along longitudinal axis X-X between reference line A and reference line F. Similar to above, a central linear segment 167 of central segment 166 may define a nominal stroke length (or "NSL") for track 160, and a proximal offshoot 172 of proximal segment 170 may define an extended stroke length (or "ESL") for track 160. As before, the NSL includes a nominal open and close operating range for end effector 16, and central segment 166 includes a plurality of central offshoots 168 configured to maintain end effector 16 in a partially open state.

In contrast to above, distal segment 162 defines an open stroke length (or "OSL") for track 160. The OSL may be used maintain end effector 16 in the fully open state and/or permit release of larger stones 3. For example, distal segment 162 of FIG. 6 comprises a distal offshoot 163 extending away from central linear segment 167 between reference lines E and F. Distal offshoot 163 comprises a distal linear segment 165 connected to central linear segment 167 by a connector segment 164. The length of distal linear segment 165 is equal to the OSL. Accordingly, pin 46 may be moved to reference line E to maintain end effector 16 in the fully open state, and then moved into distal linear segment 165 through connector segment 164 to release stone 3. For example, end effector 16 may become stuck in the fully open state when pin 46 is located at reference line E to close end effector 16 about a larger stone 3. In this example, the OSL may be used to increase the size of end effector 16, beyond that attainable at reference line E at that moment, allowing the release of stone 3.

Distal segment 162 of FIG. 6 includes a first half above longitudinal axis X-X and a second half below axis X-X. These first and second halves may be identical. Alternatively, the length of each of half may be varied to enhance the usability of device 10. For example, a first length of the first half may be equal to the OSL, while a second length of the second half is longer than the first length to enable temporary capture and/or release of stones 3 that are otherwise too large for removal with device 10. For example, pin 46 may be temporarily located in the second half to reposition a larger stone 3 in body cavity 4, permitting subsequent treatments to reduce the size of stone 3, and/or the risk that stone 3 will become stuck in end effector 16.

An exemplary device 110 is depicted in FIG. 7 as combining a housing 120 with aspects of track 160 of FIG. 6. Housing 120 is identical to housing 20, but for the replacement of track 60 with track 160. Similar to FIG. 6, track 160 of FIG. 7 comprise a plurality of segments, including distal segment 162, central segment 166, and proximal segment 170. The interaction between pin 46 and track 160 may be modified in the FIG. 7 example, wherein, pin 46 may located at: (i) distal segment 162 to maintain end effector 16 in a fully open state; (ii) one of four central offshoots 168 within central segment 166 to extend end effector 16 into a fully open state; (iii) one of the three remaining central offshoots 168 to extend end effector 16 into a corresponding one of three partially open states; and (iv) proximal segment 70 to retract end effector 16 into a fully closed state, and/release the stone 3. Similar to above, distal segment 162 includes a distal offshoot 163 that defines an open stroke length (or "OSL") for track 160. The OSL of FIG. 7 is equal to a length 14L of wire 14 that is located proximal of end effector 16, yet distal of the distal end of sheath 30, allowing pin 46 to travel back and forth in a proximal-distal direction through distal offshoot 163 of track 160.

Because end effector 16 of FIG. 7 is fully expanded once pin 46 is located in distal offshoot 163, a reciprocal extension and retraction motion of wire 14 and/or end effector 16 along length 14 may be achieved by moving pin 46 back and forth in distal offshoot 163, allowing for manipulation of stone 3 without manipulation of sheath 30. For example, pin 46 may be rapidly moved back and forth in distal offshoot 163 to pulsate stone 3. The pulse frequency, in this example, may be determined entirely by hand forces applied to device 110 by the user. These movements may be particularly useful when device 110 is coupled to a scope by a scope adaptor, and configured for operation by a single user.

Figure 8:
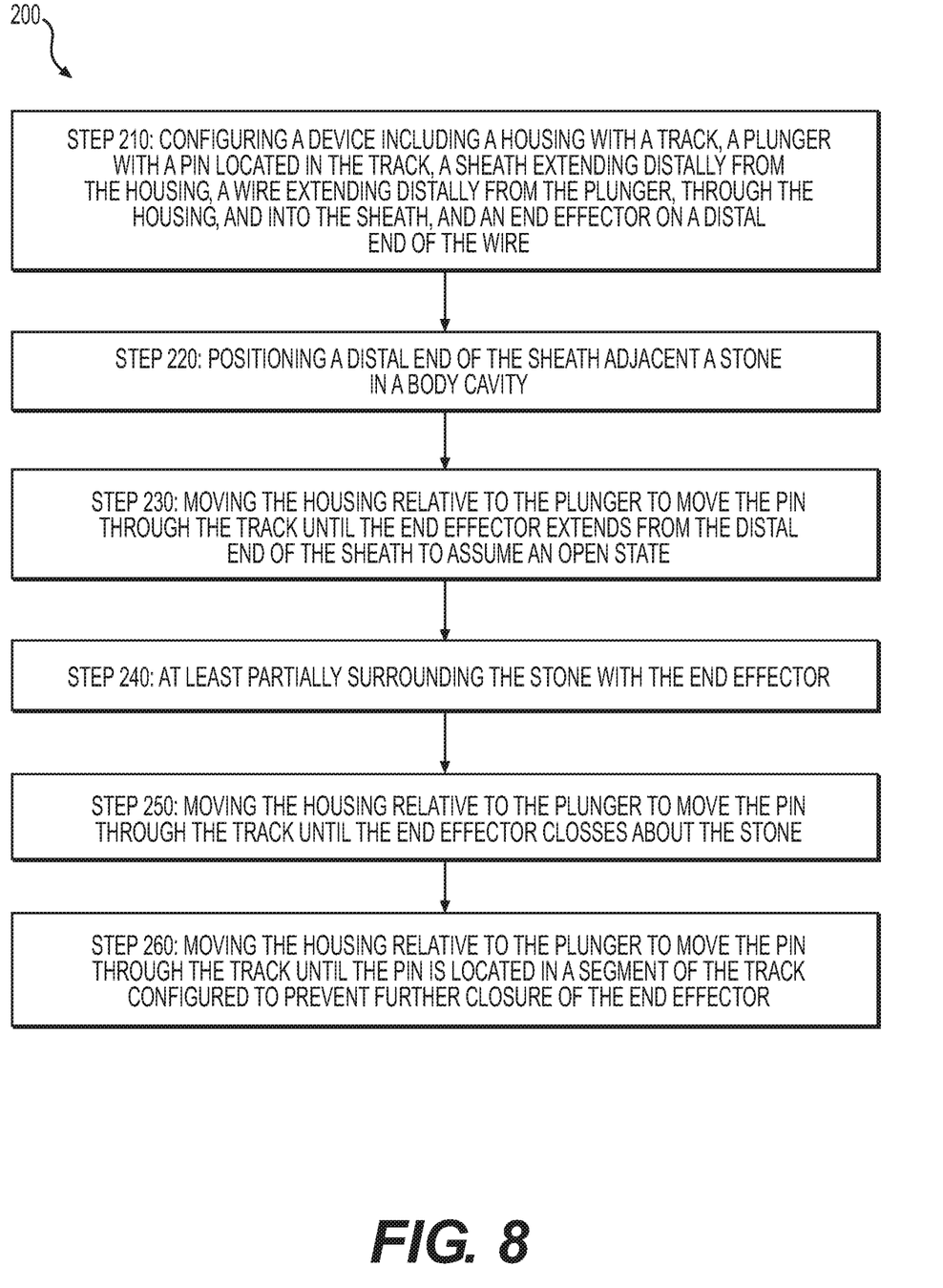
FIG. 8 depicts an exemplary method of stone capture.

An exemplary method 200 of using device 10 is now described. As shown in FIG. 8, method 200 may comprise: configuring device 10 (a configuring step 210); positioning the distal end 30D of sheath 30 adjacent stone 3 (a positioning step 220); moving housing 20 relative to plunger 40 to move pin 46 through track 60 until end effector 16 extends from the distal end of the sheath 30 to assume an open state (an opening step 230); at least partially surrounding stone 3 with end effector 16 (a surrounding step 240); moving housing 20 relative to plunger 40 to move pin 46 through track 60 until end effector 16 closes about stone 3 (a closing step 250); and moving housing 20 relative to plunger 40 to move pin 46 through track 60 until pin 46 is located in a segment of track 60 configured to prevent further closure of end effector 16 (a maintaining step 250). Additional aspects of method 200 are now described.

Configuration step 210 may include any intermediate steps required to prepare device 10 for use. For example, step 210 may comprise attaching device 10 to an insertion device, such as a scope. Device 10 may be provided in a kit including housing 20, plunger 40, one or more lengths of wire 14, each including an end effector 16; a length of sheath 30; and/or removable handle 90, and step 210 may comprise assembling device 10. An exemplary kit also may include the scope adapter described above. The kit may be sterilized in advance and sealed, and/or step 210 may include a sterilizing step. Any portion of step 210 may be performed in advance, and at manufacturing facility, and thus not performed by the user. For example, step 210 may consist essentially of grasping device 10 and/or handle 90.

Positioning step 220 may include any intermediate steps for advancing sheath 30 through body path 2 and/or locating sheath 30 in body cavity 4, such as locating interior cavity 4, and/or advancing sheath 30 through the working channel 17 of an insertion device until distal end 30D is adjacent stone 3.

Opening step 230 may include any intermediate steps for moving end effector 16 into a fully or partially open state. Relative movements between housing 20 and plunger 40 within step 230 may be guided by track 60 or 160. For example, step 230 may comprise moving pin 46 through track 60 from seat 71 of proximal segment 70 into a central offshoot 68 of central segment 66 to extend end effector 16 from sheath 30, and/or maintain end effector 16 in the open state. With track 160, for example, step 230 may further comprise advancing pin 46 into connector segment 164 and/or distal linear segment 165.

Surrounding step 240 may include any intermediate steps for positioning stone 3 within end effector 16. For example, step 240 may include moving housing 20 independent of and/or together with plunger 40 so as to move end effector 16 relative to sheath 30 until stone 3 is positioned inside of an interior portion of end effector 16. Surrounding step 240 also may include determining the size of stone 3. For example, step 240 may comprise moving housing 20 relative to plunger 40 to move pin 46 into the central offshoot 68 located at reference line C so that end effector 16 may assume a partially open state with a predetermined size; comparing the predetermined size of end effector 16 to stone 3; adjusting the size of end effector 16 responsive to the comparison by moving housing 20 relative to plunger 40 to move pin 46 through track 60 to another central offshoot 68 (e.g., at any of reference lines D-F); and positioning stone 3 within end effector 16. Similar steps may be performed to realize any aspect of end effector 16 described herein. Central offshoots 168 of track 160 of FIG. 6 may be similarly used in step 240.

Closing step 250 may include any intermediate steps for closing end effector 16 around stone 3. For example, step 250 may include moving housing 20 relative to plunger 40 to move pin 46 through track 60 until end effector 16 is at least partially retracted into sheath 30, causing the wires of end effector 16 to at least partially close upon stone 3. For softer stones 3, step 250 may comprise moving pin 46 into the central offshoot 68 located at reference F so that end effector 16 may assume the partially open state corresponding therewith; comparing the fit of stone 3 within end effector 16; and moving pin 46 to successive central offshoots 68 (e.g., from reference line F to E) until stone 3 is secured in end effector 16.

Each central offshoot 68 may correspond with a different open or closed state of end effector 16. For example, closing step 250 may include moving pin 46 through track 60 into successive central offshoots 68 to gradually move end effector 16 into successive partially open states, allowing end effector 16 to gradually close around a softer stone. If a hand force is used to move housing 20 relative to plunger 40, then this configuration may reduce the risk of unintentionally shattering the stone by allowing the hand force to be gradually applied a controlled manner.

Maintaining step 260 includes any intermediate steps for preventing further closure of end effector 16 and/or application of closure forces to stone 3, such as moving housing 20 relative to plunger 40 to fix the position of end effector 16 relative to sheath 30. For example, step 260 may comprise rotating plunger 40 relative to housing 20 so as to move pin 46 into one of central offshoots 68.

Method 200 may comprise additional method steps to aid in the capture and release of stone 3. For example, the length of central linear segment 67 may be insufficient to permit closure of end effector 16 when sheath 30 is in a tortuous configuration due to the resulting offset between sheath 30 and wire 14. Accordingly, if sheath 30 is in a more tortuous configuration, then method 200 may comprise moving housing 20 relative to plunger 40 until pin 46 is moved out of seat 71 and into proximal offshoot 72 along the ESL, causing end effector 16 to assume the fully closed state within sheath 30. As a further example, end effector 16 may become stuck in the fully open state when pin 46 is located at reference line E to close end effector 16 about a larger stone 3. Track 160 may be utilized to aid in releasing the larger stone, as described above. Accordingly, method 200 may comprise moving housing 20 relative to plunger 40 until pin 46 is moved out of central linear segment 167 and into distal linear segment 165 along the OSL, causing end effector 16 to assume a fully open state with an open size larger than that attainable when pin 46 is located central segment 167 along the NSL, and allowing the larger stone 3 to be released.

Although not required, device 10 may include a resilient element 80 mounted between housing 20 and plunger 40 (e.g., over portions of plunger 40, under portions of housing 20), as shown in FIG. 3A. Resilient element 80 may be a spring configured to apply a biasing force that biases housing 20 away from plunger 40, and/or maintains end effector 16 in a fully closed state within sheath 30. Resilient element 80 may be compressed by applying a hand force to handle 24 that is greater than the biasing force, and expanded (e.g., to return pin 46 to seat 71) when the hand force is released.

The biasing force applied to housing 20 and plunger 40 by resilient element 80 is directly proportionality to a closure force applied to stone 3 by end effector 16. The biasing force may be a linear biasing force (e.g., one that follow Hooke's Law) so that the closure force varies depending upon the location of pin 46 in track 60. For example, element 80 may be a compression spring. Alternatively, the biasing force may be a non-linear biasing force so that the closure force is constant no matter where pin 46 is located in track 60. For example, element 80 may be a constant force spring. The various segments and/or offshoots of track 60 described herein may be used to maintain end effector 16 in an open or partially open state by providing a means of limiting the closure force and/or preventing element 80 from returning pin 46 to seat 71. For example, the biasing force from element 80 may be applied to central offshoot 68 when pin 46 is located therein, allowing end effector 16 to retain stone 3 without applying the closure force thereto.

Numerous benefits may be realized with resilient element 80. For example, resilient element 80 may be used to assist closure of end effector 16 when set with a low initial biasing force. If a hand force is used to move housing 20, then this configuration may provide the user with additional tactile feedback. Resilient element 80 may be further configured to increase the durability of device 10 by limiting the closure force applied to stone 3, thereby preventing damage to end effector 16 and/or unwanted compression of sheath 30.

Resilient element 80 may be selected based on the largest stone 3 that can be captured with device 10. For example, if resilient element 80 is a compression spring, then element 80 may need to be fully compressed in order to fully open end effector 16, meaning that a maximum amount of closure force will be applied to stone 3 once element 18 is released. Wire 14 and/or end effector 16 may have a break force determined based on their respective cross-sectional dimensions and material properties. Resilient element 80 may be selected such that the maximum closure force applied to stone 3 is less than the break force of wire 14 and/or end effector 16.

Resilient element 80 also may be incorporated into device 110 of FIG. 7. In this example, as described above, pin 46 may be moved back and forth in a distal offshoot 163 to pulsate stone 3 at a pulse frequency. Element 80 may be used to modify the pulse frequency by compelling pin 46 into a proximal-most position within distal offshoot 63 whenever the hand force is removed. Aspects of resilient element 80 may be modified for use with device 110. For example, a portion of resilient element 80 may be configured to provide more or less biasing force once pin 46 enters distal portion 163, and/or be further configured to vibrate pin 46 back and force in distal offshoot 163 responsive to an initial or intermittent hand force. In other aspects, device 110 of FIG. 7 may include an actuator (e.g., a piezoelectric and/or acoustic actuator) coupled to resilient element 80, and said actuator may be used to further modify said pulse frequency by applying a vibratory force to resilient element 80.

Any aspect of method 200 may be modified to accommodate aspects of resilient element 80, track 160, and/or device 110. For example, as end effector 16 closes about stone 3 in closing step 250, the biasing force applied by resilient element 80 (e.g., if a compression spring) may diminish as it expands towards an equilibrium state. Accordingly, closing step 250 may comprise moving pin 46 between offshoots 68 to gradually decrease the closure force applied to stone 3. For example, each central offshoot 68 may correspond with a predetermined amount of closure force, allowing the user to gradually decrease the closure force until a smaller or softer stone 3 is secured in end effector 16 with minimal risk of unintended shatter. Any step of method 200 may be likewise modified to accommodate track 160 of device 110. For example, subsequent to maintaining step 250, method 200 may further comprise: a capturing step, wherein stone 3 is captured in end effector 16 by moving housing 120 relative to plunger 30 to move pin 46 back and forth in distal offshoot 163. Method 200 may further comprise a manipulation or treatment step, wherein pin 46 is moved back and forth by resilient element 80 (and/or a vibratory force applied thereto) at a pulse frequency configured to manipulate and/or treat stone 3.

Numerous aspects of devices 10 and 110 have been described with reference to relative movements between housing 20 and plunger 40 in a proximal-distal direction. It is contemplated that housing 20 may be moved relative to plunger 40, or vice versa, in any relative directions, without departing from this disclosure. For example, as described above, proximal end 40P of plunger 40 may be engaged with an insertion device, such as a scope. In this configuration, it may be easier to move housing 20 relative to plunger 40 by grasping the insertion device in one hand and handle 24 with the other, although similar benefits may be realized by moving plunger 40 relative to housing 20. As a further example, also described above, proximal end 40D may engaged with removable handle 90 and used without an insertion device. In this configuration, it may easier to move plunger 40 relative to housing 20 by grasping housing 20 with one hand and handle 90 with the other.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A device comprising:
a housing including a track with a plurality of segments;
a plunger including a pin located in the track;
a sheath extending distally from the housing;
a wire extending distally from the plunger into the sheath; and
an end effector on a distal end of the wire,
wherein the housing is movable relative to the plunger to move the pin between the plurality of segments, and each of the plurality of segments corresponds with a position of the end effector relative to the sheath,
wherein the plurality of segments comprise:
a distal segment, at which the pin is located to fully extend the end effector from the sheath;
a central segment, at which the pin is located to partially extend the end effector from the sheath, the central segment comprising a central linear segment, and the central linear segment terminating proximally in a seat; and
a proximal segment, at which the pin is located to fully retract the end effector into the sheath, the proximal segment comprising a proximal offshoot extending transverse to and proximally of the seat,
wherein the end effector assumes a fully closed state when the sheath is in a first configuration and the pin is moved into the seat, and the end effector assumes the fully closed state when the sheath is in a second configuration and the pin is moved into the proximal offshoot, wherein the second configuration is more tortuous than the first configuration.

2. The device of claim 1, wherein:
the distal segment comprises a distal offshoot transverse to and distal of the central linear segment; and
the pin is moveable into the distal offshoot to maintain the end effector in the fully open state.

3. The device of claim 1, wherein:
the central linear segment comprises at least one central offshoot extending away from the central linear segment; and
the pin is movable into the at least one central offshoot to maintain the end effector in a partially open state.

4. The device of claim 1, wherein a perimeter of the track is symmetrical about a longitudinal axis of the housing.

5. The device of claim 1, wherein the device comprises an elastic member configured to bias the housing away from the plunger.

6. The device of claim 5, wherein the elastic member is a spring configured to apply a biasing force.

7. The device of claim 1, wherein the housing is rotatable relative to the plunger.

8. The device of claim 7, wherein the housing further includes a handle, and the handle is configured to actuate the rotation of the housing relative the plunger.

9. A method of using the device of claim 1, the method comprising:
moving the housing relative to the plunger to move the pin through the track until the end effector extends from the sheath to assume an open state;
at least partially surrounding a stone with the end effector;
moving the housing relative to the plunger to move the pin through the track until the end effector closes about the stone; and
moving the housing relative to the plunger to move the pin through the track until the pin is located in a segment of the track configured to prevent further closure of the end effector.

10. The method of claim 9, wherein the device further comprises an elastic member configured to bias the housing away from the plunger, and moving the housing relative to the plunger comprises compressing the elastic member.

11. The method of claim 10, further comprising releasing the stone by moving the housing relative to the plunger to move the pin through the track until the end effector extends from the sheath to assume the open state.

12. The method of claim 11, further comprising:
advancing the sheath through a body path; and
positioning a distal end of the sheath adjacent the stone.

13. The method of claim 11, further comprising attaching the plunger to the scope.

14. A device comprising:
a plunger that includes a pin and is engageable with a wire having a distal end, the distal end of the wire including an end effector;
a housing that is engageable with a sheath, configured to receive the plunger, and includes a track having a plurality of segments;
wherein the pin is located in the track and the housing is movable relative to the plunger such that:
the pin is movable through the track to guide movement of the plunger relative the housing;
the wire extends distally from the plunger, through the housing, and into the sheath; and
each of the plurality of segments corresponds with a position of the end effector relative to the sheath,
wherein the plurality of segments comprise:
a distal segment, at which the pin is located to fully extend the end effector from the sheath;
a central segment, at which the pin is located to partially extend the end effector from the sheath, the central segment comprising a central linear segment; and
a proximal segment, at which the pin is located to fully retract the end effector into the sheath,
wherein the central linear segment terminates distally at the distal segment, and the central linear segment terminates proximally in a seat, and
wherein the end effector assumes a fully closed state when the sheath is in a first configuration and the pin is moved into the seat.

15. The device of claim 14, wherein the central segment comprises at least one central offshoot transverse to a longitudinal axis of the housing, and the pin is engageable with the at least one central offshoot to maintain the end effector in a partially open state.

16. The device of claim 15, wherein a perimeter of the at least one central offshoot is symmetrical with respect to the longitudinal axis so that the housing is rotatable in a clockwise or a counterclockwise direction relative to the plunger to locate the pin in said at least one central offshoot.

17. The device of claim 14, wherein the pin extends outwardly from a side surface of the plunger, and the side surface is configured to bias the pin toward the track.

18. The device of claim 14, wherein a proximal end of the wire is attached to a proximal end of the plunger via a lumen extending through the plunger.

19. The device of claim 18, wherein a distal end of the housing includes a handle.

20. The device of claim 14, wherein the proximal segment comprises a proximal offshoot extending transverse to and proximally of the seat, the end effector assumes the fully closed state when the sheath is in a second configuration and the pin is moved into the proximal offshoot, and the second configuration is more tortuous than the first configuration.

* * * * *